(12) United States Patent
Levine

(10) Patent No.: US 10,039,486 B1
(45) Date of Patent: Aug. 7, 2018

(54) MEANS AND METHODS FOR FACILITATING TRAUMA INTEGRATION

(71) Applicant: Peter Levine, Lyons, CO (US)

(72) Inventor: Peter Levine, Lyons, CO (US)

(*) Notice: Subject to any disclaimer, the term of this patent is extended or adjusted under 35 U.S.C. 154(b) by 0 days.

(21) Appl. No.: 15/853,814

(22) Filed: Dec. 24, 2017

Related U.S. Application Data

(60) Provisional application No. 62/446,397, filed on Jan. 14, 2017.

(51) Int. Cl.
| | |
|---|---|
| *A61B 5/02* | (2006.01) |
| *A61B 5/00* | (2006.01) |
| *A61B 5/103* | (2006.01) |
| *A61B 5/0205* | (2006.01) |
| *A61B 5/16* | (2006.01) |
| *A61B 5/08* | (2006.01) |
| *A61B 5/021* | (2006.01) |
| *A61B 5/024* | (2006.01) |
| *A61B 5/0245* | (2006.01) |

(52) U.S. Cl.
CPC .......... *A61B 5/4035* (2013.01); *A61B 5/0205* (2013.01); *A61B 5/1032* (2013.01); *A61B 5/16* (2013.01); *A61B 5/4064* (2013.01); *A61B 5/4842* (2013.01); *A61B 5/7278* (2013.01); *A61B 5/742* (2013.01); *A61B 5/7405* (2013.01); *A61B 5/021* (2013.01); *A61B 5/0245* (2013.01); *A61B 5/02405* (2013.01); *A61B 5/02416* (2013.01); *A61B 5/0816* (2013.01)

(58) Field of Classification Search
CPC ... A61B 5/4035; A61B 5/0205; A61B 5/1032; A61B 5/16
USPC ........................................................ 600/508
See application file for complete search history.

*Primary Examiner* — Amanda Hulbert
*Assistant Examiner* — Philip C Edwards
(74) *Attorney, Agent, or Firm* — Lee Weinstein

(57) ABSTRACT

An apparatus and method for diagnosing and/or treating autonomic dysregulation is disclosed. In a preferred embodiment, a user is presented stressful audio-visual content at a known time. The resulting amount of deviation of the user's autonomic nervous system from stasis is automatically quantified periodically subsequent to the presentation of the stressful audio-visual content by monitoring a parameter of the user's heartbeat over time, thus automatically measuring both the amount of disturbance in the user's autonomic nervous system, and the re-settling time of the user's autonomic nervous system for given stressful audio-visual content. The apparatus may then guide the user through one or more awareness exercises, and subsequently re-measure the user's response to stressful audio-visual content.

7 Claims, 1 Drawing Sheet

MEANS AND METHODS FOR FACILITATING TRAUMA INTEGRATION

CROSS-REFERENCE TO RELATED APPLICATIONS

This patent application is based on provisional patent application No. 62/446,397, filed Jan. 14, 2017, which is herein incorporated by reference.

FIELD OF THE INVENTION

The field of the invention relates to brain science, neurology, psychology, and more specifically to autonomic dysregulation, and therapeutic techniques for lessening the effects of past trauma, such as may currently be diagnosed under the label "post-traumatic stress disorder" (PTSD), as well as "chronic pain" and various "functional" disorders including fibromyalgia, chronic fatigue syndrome (CFS), and irritable bowel syndrome (IBS).

BACKGROUND OF THE INVENTION

A common dictionary definition of trauma is "a deeply distressing or disturbing experience". An overwhelming event may also be classified as trauma. We shall herein refer to any event which results in such an experience as a "traumatic event". We shall herein refer to any circumstances which result in trauma as "traumatic circumstances". Not all traumatic events leave an imprint which later has a disabling effect (such as PTSD). To the contrary, many perceived threatening events serve to strengthen animals or persons who go through such events. Trauma researchers such as Peter Levine (author of "In an Unspoken Voice", ISBN #1556439431, which is herein incorporated by reference) and Robert Scaer (author of "The Trauma Spectrum", ISBN #0393704661, which is herein incorporated by reference) list an abundance of research pointing to the difference between whether or not trauma results in disabling effects being determined largely by the difference between whether or not the trauma is "integrated" subsequent to the traumatic circumstance.

Within this document, traumatic memories will be considered not to be integrated if circumstances which trigger such memories result in an autonomic nervous system response which is experienced as partially or largely disabling by the person in which the response is happening (see Levine 2014, Trauma and Memory, Brain and Body in a Search for the Living Past). Since traumatic memories are typically stored in implicit memory (the memory mechanism used to remember body sensations and movements, such as "how to balance while riding a bicycle", or "how to throw a ball") rather than explicit memory (the kind of symbolic memory used to remember stories and facts), traumatic memories are often not accessible through talk therapy. In recent years, body-centered therapeutic techniques such as Somatic Experiencing and The Alexander Technique have proved themselves valuable to therapists seeking to aid clients in integrating traumatic memories.

Some of the ways in which unintegrated trauma is partly disabling to an individual may be externally measured objectively, as well as being experienced subjectively internally by the individual with unresolved trauma. For example, research has shown that for a person with unintegrated trauma, a stressful event often results in such person's autonomic nervous system taking considerably longer to return to baseline levels of sympathetic nervous system activation and parasympathetic nervous system activation, compared with the time it takes the autonomic nervous system of a person without such unintegrated trauma to return to baseline levels after such a stressful event.

In this document, we shall refer to the time it takes the autonomic nervous system (ANS, composed of sympathetic nervous system and parasympathetic nervous system) to return to within a predetermined tolerance of baseline levels after a given stressful event or series of events as the "re-settling time" for that event or series of events. Parameters such as heartrate and vagal tone (also called heart rate variability or HRV (which may be measured with or without correlation to measured respiration)) may be used as measures of activation of the central nervous system, and the term "re-settling time" may be applied to such parameters.

When heart rate variability is measured correlated to respiration, a respiration monitoring device such as a chest band may be used to measure respiration, and the difference between maximum heart rate and minimum heart rate within the time interval of one breath may be measured. When heart rate variability is measured without correlation to respiration, the difference between maximum heart rate and minimum heart rate within a period likely to be longer than the period of a typical breath can be measured.

Within this document, when we refer to "re-settling time" with respect to a parameter such as heart rate or vagal tone, it shall be assumed that we are referring to the time it takes the measured parameter to re-settle within a pre-determined tolerance of baseline level. Re-settling time may be thought of as inversely correlated with psychological or neurological resilience, meaning that a person with longer heart rate and vagal tone re-settling time may be said to be less psychologically or neurologically resilient. (Levine 1976, 1986), Porges 2011)

In this document, any difference between the re-settling time that might be evidenced in a person with unresolved trauma (compared to a person who has no unresolved trauma) may be referred to as autonomic dysregulation or stasis. There is a need for innovative technologies that can aid individuals in reducing or eliminating autonomic dysregulation. Thus, in the terminology of this document, a person with less autonomic dysregulation has more psychological or neurological resilience.

Most (if not all) trauma involves the experience of helplessness in the face of overwhelming circumstances. Examples in the animal kingdom include an animal being cornered with no route of escape, imminent capture by a predator, imminent or actual life-threatening injury, etc. In mammals, imminently life-threatening trauma often results in the most primitive part of the brain activating portions of the brain stem, medulla, hypothalamus, autonomic nervous system, and limbic system which serve to anesthetize the animal into a "seemingly dead" state, called the "immobility response", or "tonic immobility (TI). For some animals (such as the opossum) which do not have much ability to fight off or escape from predators, the TI is the default method for surviving attacks from predators. When a predator chases or attacks a prey animal and the prey animal enters the TI state, the predator may lose interest. Some animals may also give off a foul odor during the TI state, thus making them less appealing as a meal for a predator.

If an animal in the wild survives a threatening (and potentially traumatic) circumstance in which it enters the TI state, when the animal comes out of the TI state, its body typically goes through a brief stage of trembling and shaking. The muscle actions of this shaking often mimic the muscle actions of successfully escaping from or fighting off the predator. Modern trauma theory points to these muscle actions as a key component of integrating trauma. When trauma is integrated, circumstances which trigger memory of the traumatic event will not produce an autonomic nervous system response that is experienced as disabling. Experiments show that accumulating integrated traumatic memories tends to make animals more resilient and more likely to survive challenging circumstances, while accumulating non-integrated traumatic memories tends to make animals less resilient and less likely to survive challenging circumstances.

For example, in one experiment, young chicks were divided into three groups. The first and second groups were held down, unable to move, until their bodies went into the TI state. The third group was held down and did not go into the TI state. The first group was allowed to come out of the TI state naturally, going through shaking as they came out of the TI state. The second group was prodded while in the TI state until they forcibly came out of the TI state.

The three groups were each then put in water and allowed to swim until they drowned. The first group (the group that had gone into and naturally come out of the TI state) swam by far the longest. The third group (the group that had not been traumatized) swam the second longest before drowning. The group that drowned the fastest was the second group (the group that had experienced the TI state but had not been allowed to naturally integrate the experience because they were prodded out of the TI state).

Many modern trauma researchers theorize that the reason that many people who have been through traumatic events (war, rape, auto accident, abuse by a spouse) become partly or largely disabled from living vibrant lives is because they never were able to process and integrate their trauma in a natural way. It has been shown that traditional "talk therapy" rarely enables a person to integrate past trauma. Modern trauma theory explains this deficiency of talk therapy by pointing out that in a traumatic circumstance, it is primarily the more primitive (implicit) memory system of the brain that is engaged. This type of memory system is orchestrated by the brain stem, hypothalamus, and the amygdala. Implicit memory is an exact (non-verbal, non symbolic) type of memory used for remembering muscle movements (such as the skill of riding a bicycle or playing the piano). This type of memory is orchestrated by the amygdala. On the other hand, explicit memory (language-accessible memory of events, conversations, etc.) is orchestrated by the hippocampus, which often becomes greatly inhibited and almost dysfunctional under traumatic circumstances.

The type of memory with which non-integrated traumatic experiences are stored is not accessed symbolically in a way that would enable a person to talk about it or describe it. However, these memories exist in the form of procedural memories which include body reactions and sensations—these include physiological symptoms for which people often seek medical attention; and which elude medical diagnosis. Such symptoms may include pain, muscle spasms, changes in blood circulation in various parts of the body and brain. These include mental impairment, fibromyalgia, chronic fatigue, gastrointestinal disorders, changes in endocrine system balance, allergies, and may even contribute to autoimmune diseases.

During a treatment session, there are a myriad of subtle clues that a highly skilled trauma therapist may read to gain insight into when traumatic memories are being accessed and processed. Clues that skilled trauma therapists may utilize include:

Respiration rate

Breath indicating relaxation (as observed by the pause between the end of an exhalation and the beginning of the next inhalation)

Breath indicating arousal (shorter, more shallow, upper chest breathing)

Heart rate (as observed by the pulsation of the external carotid artery at the neck)

Shifts in blood flow distribution (as observed by shifts of hand skin pallor from pale and bluish to redder, or the reverse)

Overall posture

Degree of eye-contact

Pupil dilation or constriction. Subtle changes in posture indicating impending collapse Subtle changes in posture indicating readiness for action Subtle changes in posture indicating readiness to fight or flee.

Hand and arm gestures (especially subconscious ones)

Changes in skin hue

Changes in tone and/or rhythm of voice (prosody)

Changes in speech rate

Tension in various muscles that may be visible to the therapist

Changes in speech patterns (pausing, phrases used, speaking in questions vs statements, etc.)

The skills needed on the part of a therapist to consistently and meaningfully read the myriad of subtle body clues listed above may be difficult or impossible for some people to develop, and may be challenging for those who have developed them to manifest on a consistent basis. These same clues also indicate the presence and nature of a traumatic memory being accessed and/or indicate a likely path toward integrating the traumatic memory. Thus the number of therapists who exhibit a high rate of success in helping clients fully integrate past trauma remains relatively small, while the number of people partly or largely debilitated and unable to live full and vital lives due to the lingering effects of past trauma is ever-increasing. There is a pressing need for innovative technologies which can help people integrate past trauma to free people from partial disablement and the physical symptoms which may otherwise occur in the face of traumatic memories.

Many persons who have gone through significant unintegrated trauma regularly re-experience parts of the immobility response in their daily lives, and such experiences constitute an ever-increasing accumulation of unintegrated trauma, often accompanied by deep shame. Because of shame, limited financial resources, lack of access to a skilled therapist, or some combination of these factors, many such individuals do not seek or, eventually give up on seeking a therapist who might be able to help them. There is a need for innovative technologies which can help persons without access to a skilled trauma therapist.

When a person has been through a traumatic event that has not been integrated, that person typically perceives the daily situations he or she is in differently than a person without unintegrated trauma would perceive such situations. For example, persons with unintegrated trauma will often perceive situations as containing a significant element of danger or threat, where persons without such unintegrated trauma will perceive little or no danger or threat.

Skilled trauma therapists often begin their work with a patient by assessing the differences between how the patient perceives a situation and how a typical person without unintegrated trauma perceives such a situation. Looked at from a different perspective, the skilled trauma therapist often begins by assessing a patient to determine what course of therapy would be best suited to the unintegrated trauma the patient carries.

The time needed to treat different types of unintegrated trauma can be quite varied. It is, for instance, generally agreed among trauma therapists that trauma such as sexual abuse that was experienced in formative years can require significantly more therapeutic work to integrate than the trauma of (for instance) a recently experienced car accident or rape. There is a need for innovative technologies that facilitate the assessment of patients prior to a course of trauma treatment, so as to usefully inform the choice of therapeutic techniques, and so as to facilitate the grouping of persons likely to benefit from similar exercises and likely to benefit from each other's progress in group therapy.

SUMMARY OF THE INVENTION

It is an object of the present invention to help people integrate past trauma, and thus to free people from partial disablement and the multitude of physical symptoms which may otherwise occur in the face of traumatic memories being triggered. It is a further object of the present invention to facilitate the assessment of patients prior to a course of trauma therapy, so as to usefully inform the choice of therapeutic techniques. It is a further object of the present invention to aid individuals in reducing or eliminating autonomic dysregulation, and increasing psychological, physical and neuro-biological resilience.

In a preferred embodiment, the present invention provides automated assessment of a person's level of autonomic dysregulation, and guides such person through a series of exercises which incorporate further measurements of autonomic dysregulation, to facilitate reduction in autonomic dysregulation, and increase psychological and neurological resilience.

In a preferred embodiment, in the first stage in which a person interacts with the present invention, autonomic dysregulation is measured by first automatically measuring baseline heartrate, and automatically mathematically deriving baseline heartrate variability correlated with respiration. The person is then presented with an automatically controlled stressful situation (such as a frustrating game or puzzle or other emotionally stressful video presented through a computer audio/video interface, or intense physical activity), and any change in the person's heartrate and heartrate variability (also known as HRV or vagal tone) due to the automatically controlled stressful experience are measured (such measure may herein be referred to as a measure of stress-susceptibility), and the re-settling times of heartrate and vagal tone are measured, and shall herein be referred to as "baseline re-settling times".

In preferred embodiments, emotionally stressful AV content may be interactive (such as a frustrating game), or passive, such as situational immersive AV content such as virtual reality AV content, containing a circumstance known to be emotionally triggering for a user, such as an authority figure becoming angry, or other seemingly dangerous situation, or AV content of another person being abused, or other content known to trigger autonomic dysregulation for the user.

In a preferred embodiment, in the second stage in which a person interacts with the present invention, the person is given a sequence of awareness exercises to do, and the person is directed to pay attention to his or her body sensations in specified ways.

In a preferred embodiment, in the third stage in which a person interacts with the present invention, the person is again presented with an automatically controlled stressful situation. Any change in heartrate and vagal tone due to the automatically controlled stressful situation are measured, and the re-settling time for heartrate and vagal tone are measured, and compared to baseline re-settling times.

In a preferred embodiment, in the fourth stage in which a person interacts with the present invention, based on the difference between baseline and current re-settling times, the person is given further awareness exercises to do, and further iterations of such third and fourth stages may ensue.

In a preferred embodiment, the timing and stress magnitude of such iteratively applied automatically controlled stressful situations may be automatically varied, to facilitate maximum reduction in re-settling times.

DETAILED DESCRIPTIONS OF SOME PREFERRED EMBODIMENTS

Figure 1:
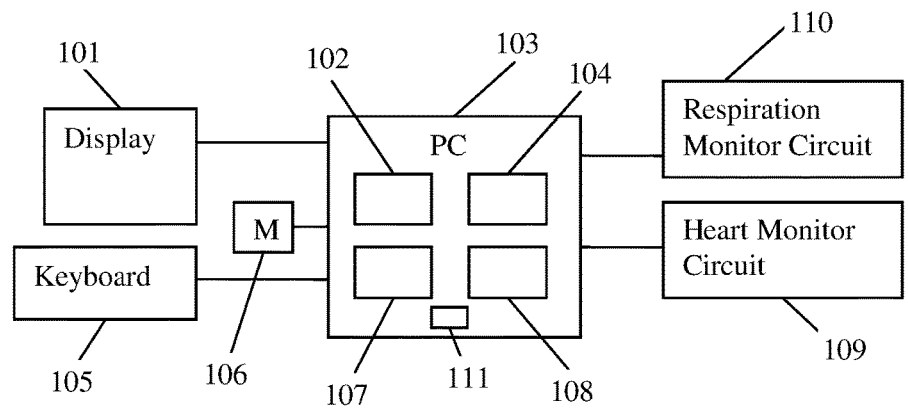
FIG. 1 is a block diagram of the hardware of a preferred embodiment of the present invention.

FIG. 1 is a block diagram of the hardware of a preferred embodiment of the present invention. In a preferred embodiment, personal computer (PC) 103 (containing random access memory (RAM) 102, non-volatile read/write memory 104 (which also acts at computer-readable non-transitory program media), central processing unit (also herein referred to as digital processor or CPU) 107, and input/output (I/O) hardware 108 (including digital input and output data interfaces) interfaces with audio/video (AV) display 101, real-time clock 111, one or more user-operable input devices such as keyboard 105 and/or mouse (or other pointing device) 106, and heart monitor circuitry 109. Heart monitor circuitry 109 may produce an analog waveform (representative of heartbeat) which is digitized in PC 103, or it may produce a digital waveform, representative of heartbeat. Any hardware within PC 103 used to digitize an analog waveform from heart monitor circuit 109 may be deemed to be part of heart monitor circuit 109 where heart monitor circuitry used is deemed to have a digital output.

The waveform produced by heart monitor circuitry 109 need not have the same shape as an electrocardiogram (ECG) waveform. The waveform could, for example, be a simple pulse train where the timing of the pulses matches the timing of a known portion of an ECG waveform or a waveform produced by an optical sensor such as a plethysmograph sensor applied to a fingertip or other body part, which acts to sense heartbeat.

In embodiments where heart rate variability is measured correlated with respiration, respiration monitor circuitry 110 interfaces to a respiration monitoring device such as a chest band or other movement sensor, and feeds an electronic signal representative of respiration to digital input/output circuitry 108.

Figure 2:
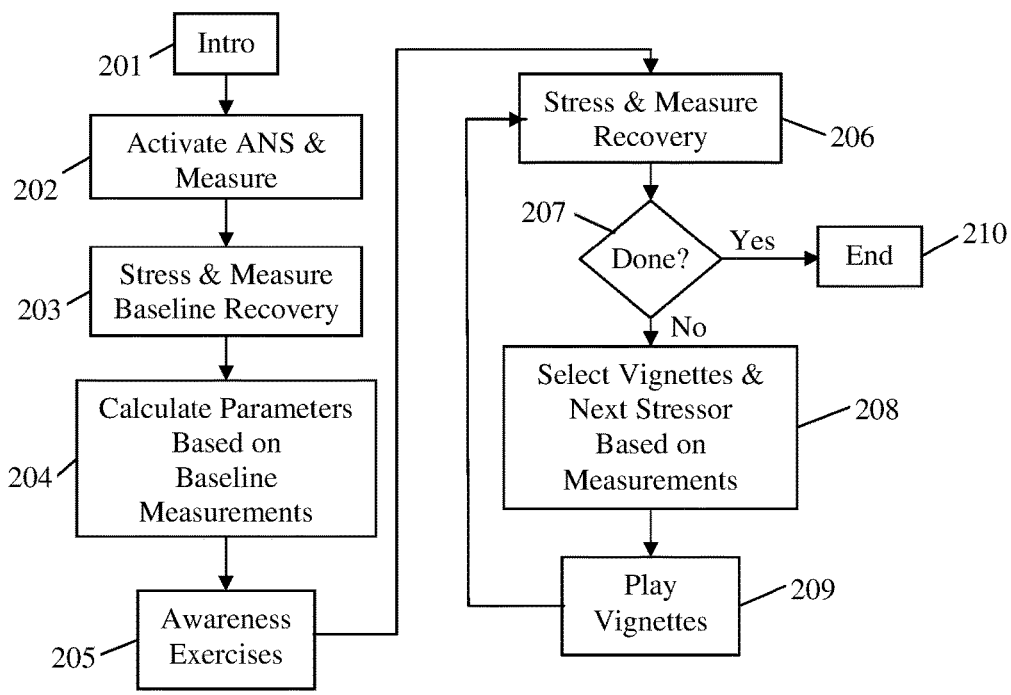
FIG. 2 is a flow chart depicting a method of operation of a preferred embodiment of the present invention.

FIG. 2 is a flow chart depicting a method of operation of a preferred embodiment of the present invention. In a preferred embodiment, in step 201, a user runs software of the present invention, which causes an audiovisual introduction to be displayed on audio-visual display (also herein referred to as AV display) 101. In preferred embodiments, AV display 101 may be a video display such as a liquid crystal display (LCD display) or other video display, or one or more loudspeakers, or one or more earphones or headphones, or any combination thereof capable of delivering audio and/or video content (also herein referred to as AV content) to a user.

The introduction may also include assessment questions asked of the user through AV display 101, and the collection of user answers to such questions through keyboard 105 and/or mouse 106. The introduction may include instructions showing the individual using the software how to hook himself or herself to heartrate monitor 109 (for instance by clipping an optical sensor to a fingertip). In a preferred embodiment, step 201 also includes automatic verification that the user has hooked himself or herself up to heartrate monitor 109 properly, and automated aid in solving any heartrate monitor functionality problems that may be encountered. Step 201 may also outline one or more of the steps or sub-steps of FIG. 2 that follow step 201.

In a preferred embodiment, in step 202, the user is presented stressful AV content to activate his or her autonomic nervous system. In one such embodiment, the user is instructed to play a frustrating game that is presented through audio/video display 101, and the frustrating game acts to activate the users autonomic nervous system. In an alternate embodiment, the user may passively watch AV content containing an unpredictable stressful event.

In an embodiment where the user interacts with a stressful game, the user may use some combination of mouse 106, keyboard 105, and/or other game input devices as may be or become known in the art, such as but not limited to joy stick devices, touch pad devices, accelerometers, etc. While the user interacts with the frustrating game, the user's heartrate is recorded over the span of time of game play (as a measure of the activation of the user's autonomic nervous system (ANS)), and game circumstances (including the user's actions in response to computer-generated game circumstances) are recorded such that heartrate changes may be correlated with circumstances within the frustrating game. Heartrate variability (HRV) correlated with respiration may also be measured as a second measure of ANS activation. Data measured in step 202 is stored in non-transitory computer-readable media. When some predetermined set of conditions involving some combination of time, and/or heartrate, and/or HRV are automatically sensed, the process moves to step 203.

In step 203, the recovery over time of the users autonomic nervous system is automatically measured through heartrate monitor 109. In a preferred embodiment, during this step, non-stressful audio/video may be presented to the user on AV display 101. In a preferred embodiment recovery time determination is made based on how long it takes the users heartrate and/or HRV to return to within a predetermined tolerance of baseline heartrate and/or baseline HRV. Data measured and results of calculations made in step 203 are stored in non-transitory computer-readable media.

In step 204 computer 103 calculates parameters based on activation measurements made in step 202, recovery measurements made in step 203, and questions answered by the user in step 201. In a preferred embodiment, one of the parameters calculated is representative of ANS resilience (or, inversely, autonomic dysregulation) of the user. In a preferred embodiment, parameters calculated in step 204 may influence content played to the user through AV 101 subsequent to step 204, and may influence timing of the presentation of such content.

In step 205, the user is automatically led through a series of awareness exercises, guided by content played on AV display 101, and the user may be queried (through AV display 101) to provide information (for instance through keyboard 105 and mouse 106) about what the user experiences during such awareness exercises.

In a preferred embodiment, in step 206, the user's autonomic nervous system is once again activated through the presentation of stressful content played through AV display 101, and subsequent to activation, the return of the user's ANS to within a predetermined tolerance of baseline levels is measured. Data measured and results of parameter calculations performed in step 206 are stored in non-transitory computer-readable media.

In decision step 207, criteria (such as total time elapsed, user-provided answers to questions, and reduction achieved in autonomic dysregulation compared to baseline) are evaluated to automatically make a decision whether to continue to step 208 or whether to end the interaction session with the user. In a preferred embodiment, if the decision is made to end the interactive session, session-ending content is played to the user through AV display 101. If the decision is made to continue the interactive session, the process proceeds to step 208.

In a preferred embodiment, in step 208, based on prior measured parameters (which may include user answers to questions) coaching/counseling vignettes are selected to be played for the user through AV display 101, and the next stressful game is selected.

In step 209, coaching/counseling vignettes selected in step 208 are played for the user through AV display 101. Subsequent to the playing of such vignettes, step 206 is re-entered with a new set of parameters calculated in step 208, and interaction continues as described above until ending step 210 is reached, or until the user terminates the interactive session with the present invention. In a preferred embodiment, the user is shown a summary of his or her progress toward decreasing autonomic dysregulation, to motivate further use of the present invention, and further progress toward decreasing autonomic dysregulation.

In embodiments of the present invention for use only in diagnosing or quantifying the severity of autonomic dysregulation, the process depicted in FIG. 2 may terminate after step 204, outputting data indicative of the level of autonomic dysregulation measured, where longer settling time for given stressful content indicates more autonomic dysregulation.

Within this document, the term "set of values" refers to one or more values.

In the foregoing description, for the purposes of illustration, methods were described in a particular order. It should be appreciated that in alternate embodiments, the methods may be performed in a different order than that described. It should also be appreciated that the methods described above may be performed by hardware components or may be embodied in sequences of machine-executable instructions, which may be used to cause a machine, such as a general-purpose or special-purpose digital processor or logic circuits programmed with the instructions to perform the methods. These machine-executable instructions may be stored on one or more machine readable non-transitory mediums, such as CD-ROMs or other types of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software. Digital results of any automated process herein may be stored in a non-transitory storage medium such as ROM, RAM, FLASH memory, magnetic disc, etc.; may be displayed visually (for instance on a computer monitor, cell phone, or other visible display); may be displayed in audio (for instance synthesized speech); or may be displayed by printing.

Specific details were given in the description to provide a thorough understanding of the embodiments. However, it will be understood by one of ordinary skill in the art that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments were described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, firmware, middleware, microcode, hardware description languages, or any combination thereof. When implemented in software, firmware, middleware or microcode, the application code or code segments to perform the necessary tasks may be stored in a non-transitory machine readable medium such as a storage medium. Operations described as being carried out by one processor may be carried out by multiple processors, and vice versa. A code segment may represent a procedure, a function, a subprogram, an application, a routine, a subroutine, a module, a software package, a class, or any combination of instructions, data structures, or application statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The foregoing discussion should be understood as illustrative and should not be considered to be limiting in any sense. While this invention has been particularly shown and described with references to preferred embodiments thereof, it will be understood by those skilled in the art that various changes in form and details may be made therein without departing from the spirit and scope of the invention as defined by the claims.

The invention claimed is:

1. An apparatus for diagnosing autonomic dysregulation, comprising:
 a computer subsystem, comprising a digital processor, an AV display, random-access memory, at least one user-operable input device, a digital input data interface, a digital data output interface, a real-time clock, non-volatile read-write memory, and a computer-readable medium containing instructions executable by said digital processor;
 heart monitoring circuitry in communication with said digital input data interface, operational to digitize at least one parameter of a user's heartbeat;
 said instructions for said processor operative to direct said processor to:
 acquire through said heart monitoring circuitry while said user is at rest a first set of values of said first parameter of said user's heartbeat, and derive from said first set of values of said first parameter a first value of a second parameter of said user's heartbeat; and
 subsequent to deriving said first value of said second parameter, output first stressful AV content through said AV display, to activate said user's autonomic nervous system; and
 while outputting said stressful AV content, acquire through said heart monitoring circuitry a second set of values of said first parameter of said user's heartbeat, and derive from said second set of values of said first parameter a second value of said second parameter of said user's heartbeat; and
 subsequent to deriving said second value of said second parameter of said user's heartbeat, terminate the output of said first stressful AV content at time $t_1$ and record the value of time $t_1$ in said random access memory; and
 subsequent to time $t_1$, monitor over time said first parameter of said user's heartbeat, periodically deriving values of said second parameter of said user's heartbeat, until said second parameter of said user's heartbeat returns to within a predetermined tolerance of said first value of said second parameter of said user's heartbeat at time $t_2$; and
 output over said digital data output interface or store in said non-volatile read-write memory data at least indicative of the time difference between $t_1$ and $t_2$.

2. The apparatus of claim 1, wherein said first heartbeat parameter comprises heart rate derived from electrocardiogram data or blood pressure waveform data or plethysmograph data or skin color fluctuation data, and said second heartbeat parameter comprises heart rate variability.

3. The apparatus of claim 1, wherein said instructions for said processor are further operative to select audio and/or video content in part based on input received from said user through said user-operable input device.

4. The apparatus of claim 1, wherein said second parameter and said first parameter are both heart rate derived from electrocardiogram data or blood pressure waveform data or plethysmograph data or skin color fluctuation data.

5. The apparatus of claim 1, wherein said instructions executable by said processor further comprise instructions to:
 subsequent to time $t_2$, output through said AV display first awareness exercise content, instructive to guide said user through a first awareness exercise; and
 subsequent to the output of said first awareness exercise content, output second stressful AV content through said AV display, to activate said user's autonomic nervous system; and
 while outputting said second stressful AV content, acquire through said heart monitoring circuitry a third set of values of said first parameter of said user's heartbeat, and derive from said third set of values of said first parameter a third value of said second parameter of said user's heartbeat; and
 subsequent to deriving said third value of said second parameter of said user's heartbeat, terminate the output of said first stressful AV content at time $t_3$ and record the value of time $t_3$ in said random access memory; and subsequent to time $t_3$, monitor over time said first parameter of said user's heartbeat, periodically deriving values of said second parameter of said user's heartbeat, until said second parameter of said user's heartbeat returns to within a predetermined tolerance of said first value of said second parameter of said user's heartbeat at time $t_4$; and;

based on the difference between the time interval between $t_1$ and $t_2$, and the time interval between $t_3$ and $t_4$, store in said non-volatile read-write memory or output through said AV display content indicative to said user of said user's progress in reducing autonomic dysregulation.

6. An apparatus for diagnosing autonomic dysregulation, comprising:

a computer subsystem, comprising a digital processor, an AV display, random-access memory, at least one user-operable input device, a digital input data interface, a digital data output interface, a real-time clock, non-volatile read-write memory, and a computer-readable medium containing instructions executable by said digital processor;

heart monitoring circuitry in communication with said digital input data interface, operational to digitize at least one parameter of a user's heartbeat;

said instructions for said processor operative to direct said processor to:

acquire through said heart monitoring circuitry while said user is at rest a first set of values of said first parameter of said user's heartbeat, and derive from said first set of values of said first parameter a first value of a second parameter of said user's heartbeat; and subsequent to deriving said first value of said second parameter, output first brief stressful AV content through said AV display at time t1, to activate said user's autonomic nervous system and record the value of time $t_1$ in said random access memory; and immediately subsequent to outputting said brief stressful AV content, acquire through said heart monitoring circuitry a second set of values of said first parameter of said user's heartbeat, and derive from said second set of values of said first parameter a second value of said second parameter of said user's heartbeat; and subsequent to time $t_1$, monitor over time said first parameter of said user's heartbeat, periodically deriving values of said second parameter of said user's heartbeat, until said second parameter of said user's heartbeat returns to within a predetermined tolerance of said first value of said second parameter of said user's heartbeat at time $t_2$; and output over said digital data output interface or store in non-volatile memory data at least indicative of the time difference between $t_1$ and $t_2$.

7. The apparatus of claim 6, wherein said instructions executable by said processor further comprise instructions to:

subsequent to time $t_2$, output through said AV display first awareness exercise content, instructive to guide said user through a first awareness exercise; and subsequent to the output of said first awareness exercise content, output second brief stressful AV content through said AV display, to activate said user's autonomic nervous system at time t3 and record the value of time $t_3$ in said random access memory; and immediately subsequent to outputting said second brief stressful AV content, acquire through said heart monitoring circuitry a third set of values of said first parameter of said user's heartbeat, and derive from said third set of values of said first parameter a third value of said second parameter of said user's heartbeat; and subsequent to time $t_3$, monitor over time said first parameter of said user's heartbeat, periodically deriving values of said second parameter of said user's heartbeat, until said second parameter of said user's heartbeat returns to within a predetermined tolerance of said first value of said second parameter of said user's heartbeat at time $t_4$; and;

based on the difference between the time interval between $t_1$ and $t_2$, and the time interval between $t_3$ and $t_4$, store in said non-volatile read-write memory or output through said AV display content indicative to said user of said user's progress in reducing autonomic dysregulation.

\* \* \* \* \*